United States Patent
Breipohl et al.

(10) Patent No.: US 6,900,318 B1
(45) Date of Patent: May 31, 2005

(54) 1,4,5,6-TETRAHYDROPYRIMIDINE DERIVATIVE AS A VITRONECTIN INHIBITOR

(75) Inventors: Gerhard Breipohl, Frankfurt am Main (DE); Anuschirwam Peyman, Kelkheim (DE); Theodor Wollmann, Hattersheim (DE)

(73) Assignee: Aventis Pharma Deutscland GmbH (DE)

( * ) Notice: Subject to any disclaimer, the term of this patent is extended or adjusted under 35 U.S.C. 154(b) by 0 days.

(21) Appl. No.: 10/031,121

(22) PCT Filed: Jul. 8, 2000

(86) PCT No.: PCT/EP00/06504

§ 371 (c)(1),
(2), (4) Date: Mar. 20, 2002

(87) PCT Pub. No.: WO01/07417

PCT Pub. Date: Feb. 1, 2001

(30) Foreign Application Priority Data

Jul. 21, 1999 (EP) .............................. 99114372

(51) Int. Cl.⁷ ...................... C07D 239/16; C07D 239/42
(52) U.S. Cl. ...................... 544/332; 514/275
(58) Field of Search .......................... 544/332; 514/275

(56) References Cited

U.S. PATENT DOCUMENTS 6,313,119 B1 * 11/2001 Peyman et al. .......... 514/235.8

FOREIGN PATENT DOCUMENTS

| WO | 9532710 | 12/1995 |
| WO | 9932457 | 7/1999 |
| WO | 9937621 | 7/1999 |

* cited by examiner

Primary Examiner—Deepak Rao
(74) Attorney, Agent, or Firm—Muserlian, Lucas and Mercanti

(57) ABSTRACT

The present invention relates to ethyl (2S)-2-(naphthalene-1-sulfonylamino)-3-(4-(2-(1,4,5,6-tetrahydropyrimidin-2-ylcarbamoyl)ethyl)benzoylamino)propionate hemifumarate of formula (I), and to a process for its preparation comprising reacting 4-(2-(1,4,5,6-tetrahydropyrimidin-2-ylcarbamoyl)ethyl)benzoic acid or a derivative thereof and ethyl (2S)-3-amino-2-(naphthalene-1-sulfonylamino) propionate. The compound of formula (I) is a valuable pharmaceutical which can be used, for example, in the treatment or prophylaxis of diseases which can be influenced by inhibiting the vitronectin receptor, in particular of bone diseases such as osteoporosis. The invention furthermore relates to chemical intermediates useful for the preparation of the compound of formula (I).

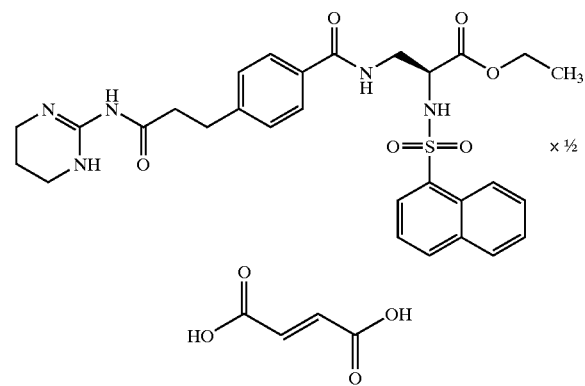

3 Claims, No Drawings

1,4,5,6-TETRAHYDROPYRIMIDINE DERIVATIVE AS A VITRONECTIN INHIBITOR

This application is a 371 of PCT/EP00/06504 filed Jul. 8, 2000.

The present invention relates to ethyl (2S)-2-(naphthalene-1-sulfonylamino)-3-(4-(2-(1,4,5,6-tetrahydropyrimidin-2-ylcarbamoyl)ethyl)benzoylamino)propionate hemifumarate of the formula I,

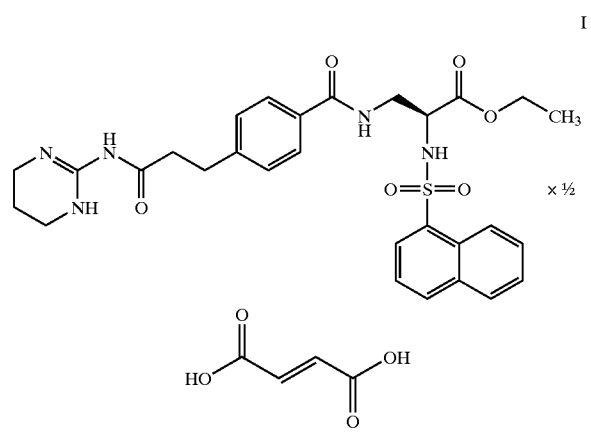

and to a process for its preparation comprising reacting 4-(2-(1,4,5,6-tetrahydropyrimidin-2-ylcarbamoyl)ethyl)benzoic acid or a derivative thereof and ethyl (2S)-3-amino-2-(naphthalene-1-sulfonylamino)propionate. The compound of the formula I is a valuable pharmaceutical which can be used, for example, in the treatment or prophylaxis of diseases which can be influenced by inhibiting the vitronectin receptor, in particular of bone diseases such as osteoporosis. The invention furthermore relates to chemical intermediates useful for the preparation of the compound of formula I.

Bones are subject to an ongoing dynamic renovation process comprising bone resorption and bone formation. In certain bone diseases like osteoporosis bone resorption predominates over bone formation thus leading to lower bone mass and enhanced fragility. Bone resorption and bone formation are controlled by types of cell specialized for these purposes. Bone resorption is based on the destruction of bone matrix by osteoclasts. Activated osteoclasts become attached to the surface of the bone matrix and secrete proteolytic enzymes and acids which cause the destruction of the bone. The attachment of osteoclasts to the bones, and thus bone resorption, is controlled by vitronectin receptors $\alpha_v\beta_3$ on the cell surface of osteoclasts. $\alpha_v\beta_3$ in this case binds to bone matrix proteins such as osteopontin, bone sialoprotein and thrombospontin. Antagonists of $\alpha_v\beta_3$ inhibit the attachment of osteoclasts to the bones and thus bone resorption as has been shown, for example, in in vivo experiments described by Fisher et al., Endocrinology 132 (1993) 1411; Yamamoto et al., Endocrinology 139 (1998) 1411; or Miller et al., Bioorg. Med. Chem. Letters 9 (1999) 1807.

The vitronectin receptor $\alpha_v\beta_3$ is a membrane glycoprotein belonging to the superfamily of integrin receptors, and besides on osteoclasts is expressed on the cell surface of other cells such as endothelial cells, cells of the vascular smooth musculature or tumor cells and controls interaction processes in which such cells are involved. In addition to inhibiting bone resorption $\alpha_v\beta_3$ antagonists are therefore capable of influencing other processes such as tumor growth and metastasis, arteriosclerosis, angiogenesis or inflammation, and in general $\alpha_v\beta_3$ antagonists are suitable for the therapy and prophylaxis of diseases which are based on the interaction between vitronectin receptors and their ligands in cell-cell or cell-matrix interaction processes or which can be prevented, alleviated or cured by influencing this interaction. $\alpha_v\beta_3$ as a therapeutic target and indications for $\alpha_v\beta_3$ antagonists are reviewed, for example, in Hillis et al., Clinical Science 91 (1996) 639; Engleman et al., Ann. Rep. Med. Chem. 31 (1996) 191; or Samanen et al., Current Pharm. Design 3 (1997) 545.

For example, it has been shown by Yue et al., Pharmacol. Rev. Commun. 10 (1998) 9; or Coleman et al., Circulation Res. 84 (1999) 1268, that $\alpha_v\beta_3$ antagonists inhibit the migration of vascular smooth muscle cells and reduce neointima formation which leads to arteriosclerosis and restenosis after angioplasty.

It has also been shown that the vitronectin receptor $\alpha_v\beta_3$ is involved in the progression of a variety of types of cancer, an that $\alpha_v\beta_3$ antagonists can cause a shrinkage of tumors by inducing the apoptosis of blood vessel cells during angiogenesis and can inhibit tumor growth and tumor metastasis (see, for example, Brooks et al., Cell 79 (1994) 1157; Carron et al, Cancer Res. 58 (1998) 1930; Yun et al., Cancer Res. 56 (1996) 1268; or above-mentioned references). The combination of $\alpha_v\beta_3$ antagonists with other known antitumor treatments has been shown to act highly efficiently on tumors and metastasis (see Lode et al., Proc. Natl. Acad. Sci. USA 96 (1999) 1591).

Friedlander et al., Science 270 (1995) 1500, have described $\alpha_v\beta_3$ antagonists which inhibit the bFGF-induced angiogenesis processes in the rat eye, a property which can be used therapeutically in the treatment of retinopathies and psoriasis. Storgard et al., J. Clin. Invest. 103 (1999) 47, have described the use of $\alpha_v\beta_3$ antagonists in the treatment of arthritic diseases.

Influencing the vitronectin receptor $\alpha_v\beta_3$ or the interactions in which it is involved thus offers the possibility of influencing different disease states for whose therapy and prophylaxis there continues to be a need for suitable pharmaceutical active ingredients.

Various integrin antagonists including $\alpha_v\beta_3$ antagonists have already been described. Exemplarily there may be mentioned the compounds described in EP-A-820991, European Patent Application 99102916.6, WO-A-93/19046, WO-A-94/12181, WO-A-95/32710, WO-A-98/00395, WO-A-98/23451 or WO-A-99/32457. Certain sulfonamide derivatives which are particularly strong $\alpha_v\beta_3$ antagonists and inhibitors of bone resorption are described in International Patent Application PCT/EP99/00242 and its corresponding applications. Said sulfonamide derivatives include (2S)-2-(naphthalene-1-sulfonylamino)-3-(4-(2-(1,4,5,6-tetrahydropyrimidin-2-ylcarbamoyl)ethyl)benzoylamino)propionic acid; and esters thereof. Ethyl (2S)-2-(naphthalene-1-sulfonylamino)-3-(4-(2-(1,4,5,6-tetrahydropyrimidin-2-ylcarbamoyl)ethyl)benzoylamino)propionate which in vivo is hydrolyzed to the actually $\alpha_v\beta_3$ antagonistic (2S)-2-naphthalene-1-suffonylamino)-3-(4-(2-

(1,4,5,6-tetrahydropyrimidin-2-ylcarbamoyl)ethyl) benzoylamino)propionic acid, exhibits an especially favorable pharmacological profile.

By the process of preparation described in International Patent Application PCT/EP99/00242, the ethyl (2S)-2-(naphthalene-1-sulfonylamino)-3-(4-(2-(1,4,5,6-tetrahydropyrimidin-2-ylcarbamoyl)ethyl)benzoylamino) propionate is obtained as hydrochloride salt. However, it turned out that the hydrochloride salt which in the process of International Patent Application PCT/EP99/00242 is isolated by concentrating a solution of the free ester in hydrochloric acid and subsequently lyophilizing, cannot be isolated or purified by crystallization or at least precipitation. Consequently, the hydrochloride salt of ethyl (2S)-2-(naphthalene-1-sulfonylamino) 3-(4-(2-(1,4,5,6-tetrahydropyrimidin-2-ylcarbamoyl)ethyl)benzoylamino) propionate can scarcely be used as pharmacologically active drug substance in pharmaceuticals for whose constituents the legislator stipulates precisely defined degrees of purity, and as target product in an industrial synthesis as in the processes for preparing, isolating and purifying a drug substance likewise conditions and operating procedures have to be adhered to which are precisely defined by legal guidelines. Salts of ethyl (2S)-2-(naphthalene-1-sulfonylamino)-3-(4-(2-(1,4,5,6-tetrahydropyrimidin-2-ylcarbamoyl)ethyl)benzoylamino)propionate with various other acids, too, cannot be crystallized or at least precipitated, and they similarly could thus not be prepared on an industrial scale in a feasible, cost and labor effective manner. The object of the present invention is to provide ethyl (2S)-2-(naphthalene-1-sulfonylamino)-3-(4-(2-(4-(1,4,5,6-tetrahydropyrimidin-2-ylcarbamoyl)ethyl) benzoylamino)propionate in a suitable form which allows an easy isolation and purification of the compound and which makes it possible to adhere with ease to the required degrees of purity and meet the demands associated with an industrial synthesis, as well as the galenic demands.

This object is achieved, surprisingly, by providing the hemifumarate salt of ethyl (2S)-2-(naphthalene-1-sulfonylamino)-3-(4-(2-(1,4,5,6-tetrahydropyrimidin-2-ylcarbamoyl)ethyl)benzoylamino)propionate which contains the ethyl (2S)-2-(naphthalene-1-sulfonylamino)-3-(4-(2-(1,4,5,6-tetrahydropyrimidin-2-ylcarbamoyl)ethyl) benzoylamino)propionate and fumaric acid in a molar ratio of 2:1 (or approximately 2:1), i.e. which contains ½(=0.5) (or approximately ½) mol of 0.5 fumaric acid per-mol of ethyl (2S)-2-(naphthalene-1-sulfonylamino)-3-(4-(2-(1,4,5,6-tetrahydropyrimidin-2-ylcarbamoyl)ethyl)benzo ylamino) propionate. Thus, a subject of the present invention is ethyl (2S)-2-(naphthalene-1-sulfonylamino)-3-(4-(2-(1,4,5,6-tetrahydropyrimidin-2-ylcarbamoyl)ethyl)benzoylamino) propionate hemifumarate of the formula I.

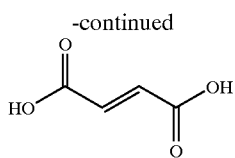

The specific salt of the formula I possesses advantageous physicochemical properties like non-hygroscopicity and stability which could not be foreseen. It can be easily isolated by precipitation, for example from the reaction solution obtained in the synthesis process, and if a purification is desired it can be precipitated under defined conditions, for example from a solution in ethanol. The compound thus fullfils the legal and technical demands on a drug substance.

The compound of the formula I can be prepared according to conventional procedures for the preparation of acid addition salts by combining the free ethyl (2S)-2-(naphthalene-1-sulfonylamino)-3-(4-(2-(1,4,5,6-tetrahydropyrimidin-2-ylcarbamoyl)ethyl)benzoylamino)propionate which may be obtained as an in situ intermediate as described in International Patent Application PCT/EP99/00242, with about 0.5 mol of fumaric acid per mol or an appropriate excess, for example about 0.55 or 0.6 mol of fumaric acid per mol, in a solvent or diluent, or it can be prepared from another salt of ethyl (2S)-2-(naphthalene-1-sulfonylamino)-3-(4-(2-(1,4,5,6-tetrahydropyrimidin-2-ylcarbamoyl)ethyl) benzoylamino)propionate which may be obtained as an synthetic intermediate, by anion exchange. Preferably the compound of the formula I is prepared by a process which comprises a new synthetic strategy for the preparation of ethyl (2S)-2-(naphthalene-1-sulfonylamino)-3-(4-(2-(1,4,5,6-tetrahydropyrimidin-2-ylcarbamoyl)ethyl)benzoylamino) propionate, followed by conversion of the latter into the hemifumarate of the formula I. This new process which provides the desired compound by a simple convergent procedure in a high yield and which is outlined in the following, is another subject of the present invention.

The new process which allows the preparation of ethyl (2S)-2-(naphthalene-1-sulfonylamino)-3-(4-(2-(1,4,5,6-tetrahydropyrimidin-2-ylcarbamoyl)ethyl)benzoylamino) propionate of the formula IV and salts thereof, in particular of the hemifumarate of the formula I, is characterized by a condensation step in which 4-(2-(1,4,5,6-tetrahydropyrimidin-2-ylcarbamoyl)ethyl)benzoic acid or a derivative thereof of the formula II and ethyl (2S)-3-amino-2-(naphthalene-1-sulfonylamino)propionate of the formula III, or a salt or salts of any one or both of these compounds, are reacted. The compound of the formula IV thus obtained can subsequently be converted into an acid addition salt by employing an acid, for example by employing fumaric acid for the preparation of the compound of the formula I.

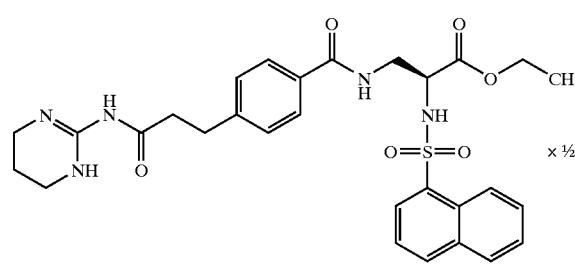

I

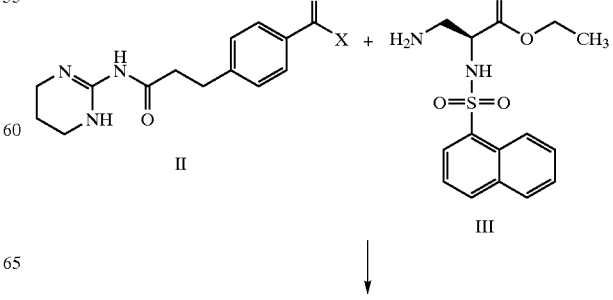

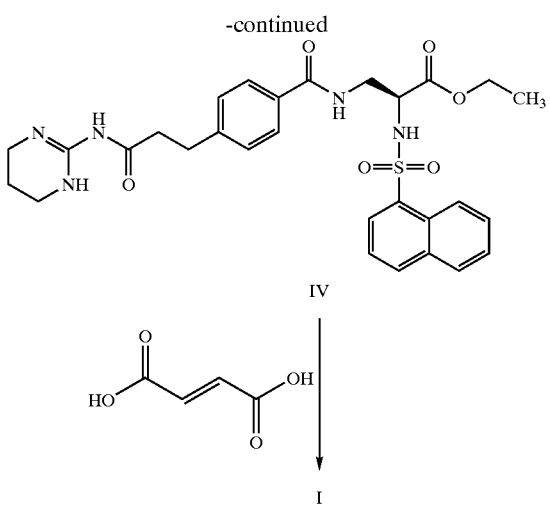

The group COX in the compounds of the formula II can be the carboxylic acid group COOH or a reactive carboxylic acid derivative, for example a carboxylic add halide such as the carboxylic acid chloride or the carboxylic acid bromide, a reactive carboxylic acid ester like an appropriate aryl ester such as the phenyl ester, the p-nitrophenyl ester or the pentafluorophenyl ester, a carboxylic acid azolide such as the imidazolide, or a group which usually is present only as an intermediate in solution like a mixed anhydride, for example a mixed carbonic acid anhydride obtained from the carboxylic acid and isobutyl chloroformate, or an activated ester like the 1-hydroxybenzotriazolyl ester or N-hydroxysuccinimidyl ester. X in the formula I thus can be hydroxy or a leaving group, for example, hydroxy, chlorine, bromine, unsubstituted or substituted phenyl, isobutoxycarbonyloxy, etc. Preferably X is hydroxy or chlorine, more preferably chlorine.

Salts as which the compounds of the formulae II and III may be employed in the reaction can be, for example, hydrohalides such as the hydrochloride or hydrobromide, salts with other inorganic acids like sulfuric acid, or salts with organic carboxylic acids or sulfonic acids like trifluoroacetic acid or p-toluenesulfonic acid. It may be advantageous to employ a compound of the formula II and/or a compound of the formula III in the form of a salt because in their preceding preparation the compounds of the formulae II and/or III are obtained as a salt and an additional step is to be avoided, and/or the salt can easier be handled in an industrial process, and/or the salt is more stable than the respective free compound. For example, if in the preceding preparation of the compound of the formula III the ethyl ester group is obtained from the respective carboxylic acid by esterification with ethanol in the presence of an acid like hydrogen chloride or sulfuric acid, the compound of the formula III is obtained as acid addition salt on the amine moiety with that acid, and moreover as such a salt the compound of the formula III is more stable during storage than the free amine. Similarly the compound of the formula II in which X is chlorine, for example, may be obtained in its preceding preparation in the form of the hydrochloride salt of the guanidine moiety, and as such a salt may be more stable and easier to handle. Preferably the compound of the formula III is employed in the reaction with the compound of the formula II as a salt, in particular as the hydrochloride salt. In case X is chlorine or bromine the compound of the formula II, too, is preferably employed as the respective hydrohalide salt, for example as the hydrochloride salt. In case X is hydroxy the compound of the formula II may be present as an inner salt (or betaine or zwitterion) containing a negatively charged carboxylate group and a positively charged guanidinium group, which type of salt is also included in the present invention.

The reaction of the compounds of the formulae II and III to give the compound of the formula IV is performed under usual conditions for the formation of an amide from an amine and a carboxylic acid or a derivative thereof which are well known to one skilled in the art including the methods and conditions known from peptide chemistry. Details of such reactions can be found in standard references like Houben-Weyl, Methoden der organischen Chemie (Methods of Organic Chemistry), Georg Thieme Verlag, Stuttgart, 1974; or J. March, Advanced Organic Chemistry, Third Edition, John Wiley & Sons, 1985.

When the compound of the formula II in which COX is COOH is employed in the reaction it is usually first activated in situ with a common activating agent for carboxylic acids such as, for example, a carbodiimide like N,N'-dicyclohexylcarbodiimide or N,N'-diisopropylcarbodiimide, a uronium salt like O-((cyano(ethoxycarbonyl)methylen) amino)-N,N,N',N'-tetramethyluronium tetrafluoroborate (TOTU) or O-(7-azabenzotriazol-1-y)-N,N,N',N'-tetramethyluronium hexafluorophosphate (HATU), or propyl phosphonic anhydride. The activation can also be carried out to give as an in situ intermediate one of the compounds of the formula II already mentioned above, for example an imidazolide by reaction with 1,1'-carbonyldiimidazole, or a mixed carbonic anhydride by reaction with an alkyl chloroformate, or an acid halide like the acid chloride by reaction with a chlorinating agent such as thionyl chloride or oxalyl chloride. The activation can be performed under standard conditions. For example, the activation with an alkyl chloroformate, a carbodiimide or a uronium salt is usually carried out in an inert aprotic solvent, for example a hydrocarbon or chlorinated hydrocarbon like toluene or dichloromethane, an ether like tetrahydrofuran, dioxane or dimethoxyethan, an ester like ethyl acetate, an amide like N,N-dimethylformamide or N-methylpyrrolidone or a nitrile like acetonitrile, or a mixture of such solvents, at temperatures from about −10° C. to about room temperature. The activated carboxylic acid is then reacted with the compound of the formula III, usually at temperatures from about −10° C. to about room temperature. Usually the activation and the subsequent reaction with the compound of the formula III are carried out in the presence of a base like, for example, a tertiary amine such as triethylamine, N,N-diisopropylethylamine or N-methylmorpholine which base also liberates the free amine of the formula III in case a salt thereof is employed, and ensures that finally the free compound of the formula IV is present. The mentioned bases and solvents like the mentioned hydrocarbons, ethers, amide or nitriles may also be used when a compound of the formula II in which COX is a carboxylic acid ester is reacted with the compound of the formula III or a salt thereof, such a reaction usually being carried out at temperatures from about 0° C. to about 80° C.

When a compound of the formula II is employed in which X is chlorine or bromine, in particular chlorine, besides in solvents like hydrocarbons or chlorinated hydrocarbons such as toluene, chloroform or dichloromethane ethers such as tetrahydrofuran, dioxane or dimethoxyethan, esters such as ethyl acetate, amides like N,N-dimethylformamide or N-methylpyrrolidone or nitriles such as acetonitrile, or mixtures of such solvents, the reaction can also be carried out in water or a mixture of one or more of the mentioned solvents and water, and particularly favorably it is carried out in a two phase system of water and an organic solvent which is substantially immiscible with water, for example in a mixture of a hydrocarbon or chlorinated hydrocarbon, for example dichloromethane, and water or in a mixture of an ester, for example ethyl acetate, and water.

In order to obtain the free compound of the formula IV a compound of the formula II in which X is chlorine or bromine is usually reacted with a compound of the formula III in the presence of a sufficient amount of a base which scavenges the hydrogen halide that is produced in the reaction, and which also liberates the free amine in case a salt of the compound of the formula III is employed. Besides tertiary amines like, for example, triethylamine or pyridine also inorganic bases can favorably be used, for example hydrogen carbonates like sodium hydrogen carbonate or potassium hydrogen carbonate, carbonates like lithium carbonate, sodium carbonate, potassium carbonate, cesium carbonate, magnesium carbonate or calcium carbonate, or hydroxides like sodium hydroxide, potassium hydroxide or calcium hydroxide, or mixtures of such bases. In particular when the reaction is carried out in the presence of water the use of an inorganic base is preferred. Depending on the intended technical details of a reaction of a compound of the formula II in which X is chlorine or bromine with a compound of the formula III, certain bases and certain modes of introducing the base into the reaction mixture are particularly advantageous. For example, in case a hydrogen carbonate is to be used in a two phase system it may be preferred to introduce the whole amount of the base at the beginning whereas in case a hydroxide is to be used it may be preferred to add the base gradually during the course of the reaction. It may also be favorable to add the base in such a manner that a certain pH range, for example a pH from about 5 to about 10, in particular from about 7 to about 9, is maintained during the reaction of a compound of the formula II in which X is chlorine or bromine with a compound of the formula III.

The reaction of a compound of the formula II in which X is chlorine or bromine with a compound of the formula III is usually carried out at temperatures from about 0° C. to about 40° C., preferably at temperatures from about 10° C. to about 30° C., in particular at about room temperature.

In general, depending on the specific mode of reaction the molar ratio of the compounds of the formulae II and III is usually from about 1.1:1 to about 1:1.1, preferably about 1:1. The compound of the formula II can be initially introduced, in particular if the compound of the formula II is employed in which X is hydroxy and which first is to be activated, and the compound of the formula III subsequently be added in one or several portions or continuosly. Just so, the compound of the formula III can be initially introduced and the compound of the formula II can be added in one or several portions or continously, or both components can also be metered simultaneously into the reaction vessel. The compounds of the formulae II and III can be employed in the form of solutions or suspensions or as solids. Depending on the details of the reaction, the reaction of the compounds of the formulae II and III is usually complete soon after mixing of the reactive components, and stirring of the reaction mixture usually needs to be continued not longer than for a few hours, for example 0.5 to 8 hours.

The workup of the reaction mixture depends on the specific manner in which the reaction is performed. In general, workup can be carried out using conventional working steps like adding water and/or organic solvents, adjusting the pH, separating phases, performing extractions, washing, drying, filtering, evaporating, etc. In case the reaction of th compounds of the formula I is carried out in a water-immiscible organic solvent workup is preferably performed by adding water to give a two phase system, optionally adjusting a slightly basic pH, separating the phases, optionally extracting the aqueous phase, drying and optionally concentrating or evaporating the organic phases. In an according manner the workup is preferably performed in case the reaction is carried out in a mixture of a water-immiscible solvent and water. In case the reaction is carried out in a water-miscible organic solvent the workup is preferably performed by first removing the solvent under reduced pressure, then adding a water-immiscible solvent and water to give a two phase system and proceeding as before. In all these preferred workup procedures the free compound of the formula IV is directly obtained in the form of a solution in an organic solvent or, if in the evaporating step the solvent is completely removed, in the form of an evaporation residue which can then be dissolved in a desired organic solvent.

For the preparation of a desired acid addition salt of the compound of the formula IV the obtained solution of the compound of the formula IV is combined with the desired acid. The acid can be employed in pure form or in the form of a solution or suspension, and either the acid can be added to the solution of the compound of the formula IV, or the solution of the compound of the formula IV can be added to the acid. The preferred amount of the acid depends on the details of the specific salt formation. In case a 1:1 acid addition salt is to be prepared the acid is usually employed in a molar ratio of about 1:1 or in a molar excess from about 1.3:1 to 1:1 or from about 1.1:1 to 1:1 where usually the molar amount of the acid can conveniently be based on the molar amount of the starting compounds of the formulae II or III. In case a 2:1 acid addition salt containing two mol of the compound of the formula I per mol of acid is to be prepared the acid is usually employed in a molar ratio of about 0.5:1 (i.e. 0.5 mol of the acid per 1 mol of the compound of the formula IV) or in a molar excess from about 0.65:1 to 0:5:1 or from about 0.55:1 to 0.5:1. If the resulting salt cannot be crystallized or precipitated from the solution it is isolated by evaporation or lyophilization, and if desired the product is then subjected to purification procedures. If the salt crystallizes or can be precipitated the solvent in which the salt formation is carried out, the amount of the solvent and the temperature are preferably chosen such that the crystallization or precipitation of the product starts from a clear solution.

In case the hemifumarate of the compound of the fomula IV, i.e. the compound of the formula I, is to be prepared preferably about 0.5 mol of fumaric acid, conveniently based on the molar amount of the starting compounds of the formula II or III, is added to the obtained solution of the compound of the formula IV, for example directly to its dried and partially evaporated solution in dichloromethane if this solvent is used for the reaction of the compounds of the formulae II and III and/or for extractive workup. After combining the fumaric acid and the compound of the formula IV it may be favorable first to beat the mixture to give a clear solution, for example to about 30° C. to 40° C. If dichloromethane is used, from which solution upon cooling the compound of the formula I starts to precipitate or can be precipitated. To complete precipitation the suspension may be cooled, for example to a temperature from about −10° C. to about 5° C. or a temperature from about −5° C. to about 0° C., and/or an additional solvent may be added in which the salt is only slightly soluble. The solid hemifumarate of the formula I is then separated by filtration or centrifugation, washed, and if desired dried and/or purified. The product is obtained in high yield and high purity.

The starting compounds of the formulae II and III employed in the above reaction can be obtained as described in the following. The preparation of the ethyl (2S)-3-amino-2-(naphthalene-1-sulfonylamino)propionate of the formula III or a salt thereof may start from (S)-asparagine (=(L)-asparagine) of the formula V which is readily available in optically pure form. In the compound of the formula V the amino group is first sulfonylated under standard conditions with reactive derivative of naphthalene-1-sulfonic acid, for example with naphthalene-1-sulfonyl chloride of the formula VI, usually in the presence of a base at temperatures from about 0° C. to about room temperature. This reaction may conveniently be carried out, for example, in a mixture of an organic solvent and water, for example a mixture of tetrahydrofuran and water or of dimethoxyethane and water, using an alkali metal hydroxide as base, for example sodium hydroxide, with maintaining the pH in the alkaline range, for example at about 12. The components can usually be employed in a molar ratio of about 1:1.

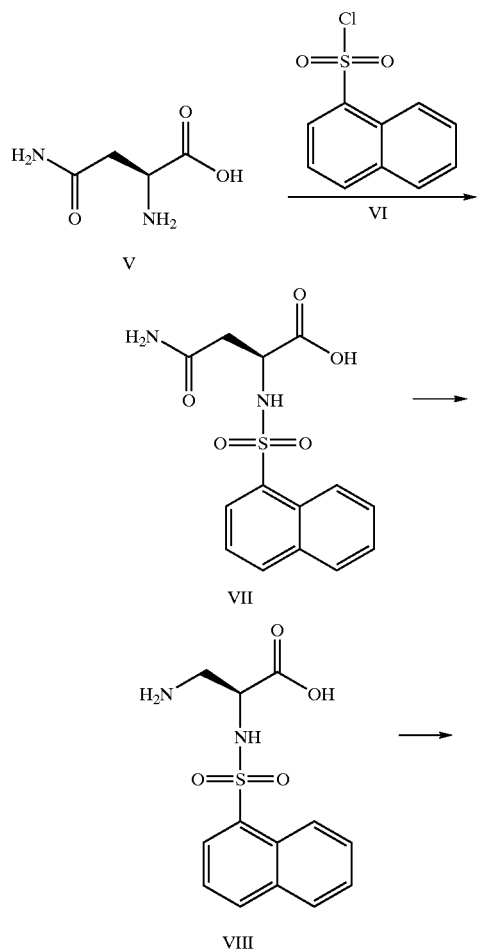

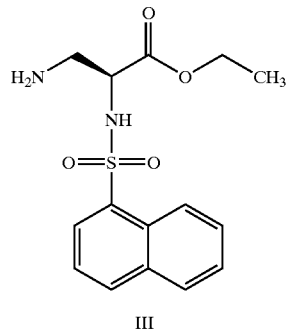

III

The carbamoyl group in the obtained succinamic acid derivative of the formula VII can then be converted into an amino group to give the 3-aminopropionic acid derivative of the formula VIII by means of a Hofmann degradation, i.e. by the action of a solution of chlorine or bromine in aqueous alkali metal hydroxide, for example sodium hydroxide or potassium hydroxide, or of an alkali metal hypohalite which is the active ingredient in such a solution. In detail the Hofmann degradation is preferably carried out substantially as described below in the example section using bromine and sodium hydroxide, following the method described by Amato et al., J. Org. Chem. 63 (1998) 9533. The product of the formula VIII may conveniently be isolated from the aqueous reaction mixture by acidification to a pH of about 6.5 to 7 at which the inner salt precipitates.

Esterification of the compound of the formula VIII to give the compound of the formula II or a salt thereof can be carried out under standard conditions, for example with ethanol in the presence of an acid catalyst like gaseous hydrogen chloride or sulfuric acid at temperatures from about 20° C. to the boiling temperature of ethanol. Preferably in the acidic-esterification process more than one equivalent of the acid is employed so that the resulting aminoester of the formula VIII is present as the respective acid addition salt which can easily be isolated and exhibits a higher storage stability. Preferably the esterification is done by passing hydrogen chloride gas into a suspension of the compound of the formula VII in ethanol and isolating the product in the form of the hydrochloride of the compound of the formula VIII.

The preparation of the 4-(2-(1,4,5,6-tetrahydropyrimidin-2-ylcarbamoyl)ethyl)benzoic acid or derivative thereof of the formula II or a salt thereof may start from commercially available formylbenzoic acid of the formula IX. Under standard conditions as described, for example, by Hu et al., Bioorg. Med. Chem. 5 (1997) 1873 the acid of the formula IX is first converted into an appropriate ester, for example with a benzyl halide like benzyl bromide into the known benzyl ester of the formula X. To achieve such an O-alkylation usually the acid and the benzyl halide are reacted in a solvent or diluent, for example in an amide like N,N-dimethylformamide, in the presence of a base like, for example, potassium carbonate at room temperature or elevated temperature. The benzyl ester of the formula X can be directly used in the subsequent step in crude form without further purification.

The ester of the formula X is then condensed with malonic acid under the conditions of the Knoevenagel reaction to give the cinnamic acid derivative of the formula XI. When carried out under the classic conditions of the Knoevenagel condensation in pyridine in the presence of piperidine under reflux the yield of the resulting compound of the formula XI is higher than 95% (based on the formylbenzoic acid of the formula IX).

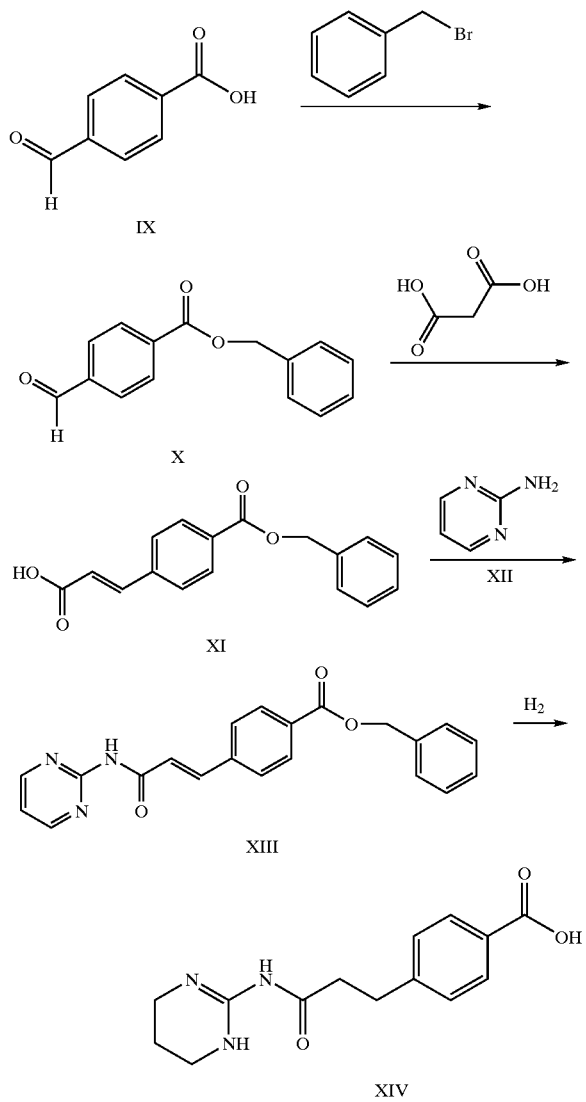

To allow a smooth reaction with 2-aminopyrimidine of the formula XII to give the benzyl 4-(2-(pyrimidin-2-ylcarbamoyl)vinyl)benzoate of the formula XIII, the carboxylic acid moiety in the compound of the formula XII is expediently first activated or converted into a more reactive carboxylic acid derivative. The above explanations with regard to the activation of the carboxylic acid of the formula II in which X is hydroxy correspondingly apply to the activation of the compound of the formula XI. In a preferred manner, the compound of the formula XI is converted into an acid halide, in particular into the acid chloride, i.e. into the compound of the formula XI in which the group COOH is replaced with the group COCl, with a chlorinating agent such as thionyl chloride or oxalyl chloride under standard conditions. The acid of the formula XI may be reacted, for example, with an excess of thionyl chloride, if desired in an inert solvent like a hydrocarbon or chlorinated hydrocarbon such as toluene, until the evolution of sulfur dioxide and hydrogen chloride ceases. Following removal of the solvent and/or the excess thionyl chloride, the crude acid chloride (or another reactive derivative of the compound of the formula XI that is employed instead of the acid chloride) is then reacted with 2-aminopyrimidine under conventional conditions for the formation of an amide. The above explanations with regard to the reaction of the compounds of the formulae II and III correspondingly apply to the present reaction. Usually the reaction is carried out in the presence of a base, in the present case in particular a tertiary amine like triethylamine or preferably pyridine, in an inert solvent or diluent such as, for example, a hydrocarbon or chlorinated hydrocarbon like dichloromethane or an ether or ester at temperatures from about −10° C. to about 20° C.

In the obtained compound of the formula XIII then the carbon carbon double bond in the CH=CH—CO—N moiety is reduced to a single bond, the heteroaromatic pyrimidin-2-yl moiety is reduced to a 1,4,5,6-tetrahydropyrimidin-2-yl moiety and the benzyl ester group is cleaved to give the 4-(2-(1,4,5,6-tetrahydropyrimidin-2-ylcarbamoyl)ethyl)benzoic acid of the formula XI. These three conversions can be achieved simultaneously in a single reaction step, namely by a catalytic hydrogenation. It is therefore preferred to proceed in the synthetic strategy of the present invention via the benzyl ester compounds of the formulae X, XI and XIII and perform the conversion of the compound of the formula XIII into the compound of the formula XIV including ester cleavage by catalytic hydrogenation.

The catalytic hydrogenation of the compound of the formula XIII or a salt thereof to the compound of the formula XIV is preferably carried out in the presence of a conventional noble metal catalyst, for example a palladium, rhodium or platinum catalyst, in particular in the presence of palladium on charcoal. The amount of the catalyst depends on the details of the reaction and the desired reaction rate and may be, for example, 0.5 to 5 mol-% (based on the compound of the formula XIII). As solvent or diluent one or more solvents like acetic acid, $(C_1–C_4)$-alcohols such as methanol, ethanol or isopropanol, in particular isopropanol, ethers such as tetrahydrofuran or dioxane, or water may be used, for example a mixture of acetic acid with one of the solvents water, isopropanol and dioxane, in particular a mixture of acetic acid and water. It is preferred to carry out the hydrogenation of the compound of the formula XIII at an acidic pH in the presence of a carboxylic acid like acetic acid which may also function as a solvent, or an inorganic acid like hydrochloric acid or sulfuric acid. Preferably a weak acid like acetic acid is employed. The choice of the hydrogen pressure depends on the available technical equipment and can be about 1 bar, or up to about 2 bar, or up to about 5 bar, or higher. The hydrogenation is usually carried out at temperatures from about 20° C. to about 60° C. After removal of the catalyst the product of the formula XIV (which also is the compound of the formula II in which X is hydroxy) is isolated by conventional methods. In case the hydrogenation is carried in the presence of a strong acid like hydrochloric acid or sulfuric acid preferably the product is completely converted into the respective acid addition salt of the compound of the formula XIV, or the acid is neutralized and the product is completely converted into the free compound of the formula XIV (which may be an inner salt).

For the preparation of a compound of the formula II in which X is chlorine or bromine the compound of the formula XIV is converted into the carboxylic acid halide by a conventional chlorinating agent, for example thionyl chloride, oxalyl chloride or oxalyl bromide. Preferably the compound of the formula XIV is converted into the acid chloride, i.e. the compound of the formula II in which X is chlorine, by reaction with an excess of thionyl chloride, for example 1.2 to 2 mol thionyl chloride per mol of the compound of the formula XIV. An excess of thionyl chloride may also be used as solvent or diluent, or an inert solvent or diluent like a hydrocarbon or a chlorinated hydrocarbon such as toluene or dichloromethane may be added which, together with the excess thionyl chloride, after completion of the reaction is removed in vacuo. The reaction is usually carried out at elevated temperatures from about 40° C. to about 100° C. The hydrogen halide that is formed during the transformation of the compound of the formula XIV into an acid halide is bound by the basic guanidine moiety in the molecule to give the hydrogen halide addition salt. The acid halide is preferably isolated in the form its solid hydrogen halide salt which can directly be employed in the reaction with the compound of the formula III as explained above.

As a whole, the above-described process for the preparation of the compound of the formula I from the compounds of the formulae II and III, taken together with the above-described processes for the preparation of the starting compounds of the formulae II and III, provides the compound of the formula I in a simple manner and in an exceptional high overall yield from readily available starting materials. Among the potential strategies for building the molecule of the formula I (or the formula IV) the unique way in which in the present process small building blocks are assembled to certain intermediates which are then combined to give the final target compound, thus proves to be particularly successful. At any rate the yield obtained in the present process is considerably higher than the yield of the compound of the formula I that would be obtainable if the process of International Patent Application PCT/EP99/00242 would be followed for the preparation of the intermediate compound of the formula IV, and the present process is simpler and better applicable on an industrial scale than that of International Patent Application PCT/EP99/00242. To a considerable amount the advantages of the present process are based on the use of the key intermediates of the formulae II and XIV, i.e. on the use of 4-(2-(1,4,5,6-tetrahydropyrimidin-2-ylcarbamoyl)ethyl)benzoic acid and its derivatives, and on the favorable process for their preparation, in particular the simple preparation of the compound of the formula XIV by hydrogenation of its precursor of the formula XIII which in one step accomplishes the removal of the benzoic acid benzyl protection group and the reduction of as well the cinnamic acid double bond as the pyrimidine ring.

A subject of the present invention are therefore also the compounds the formulae II and XIV which are valuable intermediates for the preparation of pharmacologically active compounds like the hemifumarate of the formula I or other salts of the compound of the formula IV, or of other compounds which contain a 4-(2-(1,4,5,6-tetrahydropyrimidin-2-ylcarbamoyl)ethyl)benzoyl moiety. A subject of the present invention are in particular the compounds of the formula XV,

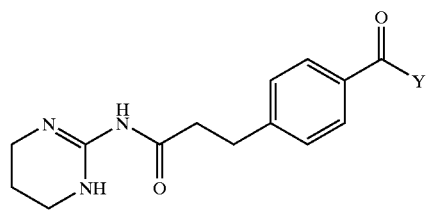

XV in which Y is hydroxy, chlorine or bromine, and their salts. Examples of salts of the compounds of the formula XV are hydrogen chloride salts or hydrogen bromide salts which may in particular be present in case Y is chlorine or bromine. The compound of the formula XV in which Y is hydroxy and which is not an acid addition salt at the guanidine moiety is also covered by the formula XV and by the present invention as an inner salt (or betaine). Preferred compounds of the formula XV are those compounds in which Y is hydroxy or chlorine, and the salts thereof, i.e. -4-(2-(1,4,5,6-tetrahydropyrimidin-2-ylcarbamoyl)ethyl)benzoic acid and 4-(2-(1,4,5,6-tetrahydropyrimidin-2-ylcarbamoyl)ethyl)benzoyl chloride and their salts, in particular the hydrochloride salt in the case of the compound of the formula XV in which Y is chlorine. Further subjects of the present invention are the above-described exceptionally simple and highly efficient process for the preparation of 4-(2-(1,4,5,6-tetrahydropyrimidin-2-ylcarbamoyl)ethyl)benzoic acid or a salt thereof by hydrogenation of benzyl 4-(2-(pyrimidin-2-ylcarbamoyl)vinyl)benzoate or a salt thereof, as well as benzyl 4-(2-pyrimidin-2-ylcarbamoyl)vinyl)benzoate of the formula XIII or a salt thereof which is the starting material for said process.

The compound of the formula I is a valuable pharmacologically active compound which is suitable, for example, for the therapy and prophylaxis of bone disorders, tumor diseases, cardiovascular disorders or inflammatory conditions. The compound of the formula I can be administered to animals, preferably to mammals, and in particular to humans as a pharmaceutical for therapy or prophylaxis. It can be administered on its own or in mixture with other pharmacologically active compounds or in the form of pharmaceutical compositions which permit enteral or parenteral administration and which, as active constituent, contain an efficacious dose of the compound of the formula I.

The present invention therefore also relates to the compound of the formula I for use as a pharmaceutical, to the use of the compound of the formula I for the production of pharmaceuticals for the therapy and prophylaxis of the diseases mentioned above or below, for example for the therapy and prophylaxis of bone disorders, and also to the use of the compound of the formula I for the therapy and prophylaxis of these diseases and to methods for such therapy and prophylaxis. The present invention furthermore relates to pharmaceutical compositions (or pharmaceutical preparations) which contain an efficacious dose of the compound of the formula I and a customary pharmaceutically acceptable carrier, i.e. one or more pharmaceutically acceptable carrier substances and/or additives.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions emulsions or tinctures, or in other ways, for example in the form of aerosols or nasal sprays.

The pharmaceutical compositions according to the invention are prepared in a manner known per se and familiar to those skilled in the art, the compound of the formula I being mixed with one or more pharmaceutically acceptable inert inorganic and/or organic carrier substances (or excipients), and/or additives and, if desired, one or more other pharmaceutically active compounds and being brought into a suitable administration form and dosage form that can be used in human or veterinary medicine. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical compositions normally contain about 0:5 to 90% by weight of the compound of the formula I. The amount of the active ingredient of the formula I in the pharmaceutical compositions normally is from about 0.2 mg to about 500 mg, preferably from about 1 mg to about 0.200 mg but depending on the type of the pharmaceutical composition it may also be higher.

In addition to the active ingredient of the formula I and carrier substances, the pharmaceutical compositions can contain additives (or auxiliary substances) such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. Furthermore, in addition the compound of the formula I, they can also contain one or more-other therapeutically or prophylactically active ingredients.

The compound of the formula I in vivo is an antagonist of the vitronectin receptor and inhibits cell adhesion. It has, for example, the ability to inhibit the binding of osteoclasts to the bone surface and thereby inhibit bone resorption by osteoclasts. The action of the compound of the formula I can be demonstrated, for example, in the test described below. Because of its vitronectin receptor antagonistic activity the compound of the formula I is generally suitable for the therapy and prophylaxis of diseases which are based on the interaction between vitronectin receptors and their ligands in cell-cell interaction processes or cell-matrix interaction processes, or which can be influenced by an inhibition of interactions of this type, or for the prevention, alleviation or cure of which an inhibition of interactions of this type is desired. As explained at the beginning, such interactions play a part, for example, in bone resorption, in angiogenesis or in the proliferation of cells of the vascular smooth musculature. The compound of the formula I is therefore suitable, for example, for the prevention, alleviation or cure of diseases which are caused at least partially by an undesired extent of bone resorption, angiogenesis or proliferation of cells of the vascular smooth musculature.

Bone diseases for whose treatment and prevention the compound of the formula I can be employed are especially osteoporosis hypercalcemia, osteopenia, for example caused by metastases, dental disorders, hyperparathyroidism, periarticular erosions in rheumatoid arthritis and Paget's disease. In addition, the compound of the formula I can be used for the alleviation, avoidance or therapy of bone disorders which are caused by a glucocorticoid, steroid or corticosteroid therapy or by a lack of sex hormone(s). All these disorders are characterized by bone loss which is based on the inequilibrium between bone formation and bone destruction and which can be favorably influenced by the inhibition of bone resorption by osteoclasts. The compound of the formula I can also favorably be used as inhibitor of bone resorption, for example in the therapy or prophylaxis of osteoporosis, in combination with conventional osteoporosis treatments such as, for example the administration of bisphosphonates, estrogens, estrogen/progesterone (hormone replacement therapy or HRT), estrogen agonists/antagonists (selective estrogen receptor modulators or SERMs), calcitonin, vitamin D analogues, parathyroid hormone, growth hormone secretagogues, or sodium fluoride (cf. Jardine et al., Annual Reports in Medicinal Chemistry 31 (1996) 211). Administration of the compound of the formula I and of other active ingredients effective in the treatment or prophylaxis of osteoporosis like those listed before can take place simultaneously or sequentially, in any order, and jointly or separately. For use in such a combination treatment or prophylaxis the compound of the formula I and one or more other active ingredients like those listed before can together be present in a single pharmaceutical composition, for example tablets, capsules or granules, or can be present in two or more separate pharmaceutical compositions which can be contained in a single package or in two or more separate packages. The use of the compound of the formula I in such a combination therapy or prophylaxis and their use in the production of pharmaceuticals for such a combination therapy or prophylaxis are also subjects of the present invention. The invention furthermore relates to pharmaceutical compositions which comprise an efficacious amount of the compound of the formula I together with at least one other active ingredient effective in the treatment or prophylaxis of osteoporosis or in the inhibition of bone resorption like those listed before, together with a customary pharmaceutically acceptable carrier. The above explanations on pharmaceutical compositions correspondingly apply to such pharmaceutical combination compositions.

Apart from use as inhibitors of bone resorption by osteoclasts, the compound of the formula I can be used, for example, as inhibitors of tumor growth and tumor metastasis, as antiinflammatories, for the therapy or prophylaxis of rheumatoid arthritis, for the therapy of psoriasis, for the therapy or prophylaxis of cardiovascular disorders such as arteriosclerosis or restenoses, for the therapy or prophylaxis of nephropathies or retinopathies such as, for example, diabetic retinopathy. As inhibitor of tumor growth or tumor metastasis the compound of the formula I can also favorably be used in combination with conventional cancer therapy. Examples of conventional cancer therapy are given in Bertino (Editor), Encyclopedia of Cancer, Academic Press, 1997 which is incorporated herein by reference. All the above statements relating to the use of the compound of formula I in combination with conventional osteoporosis therapy like, for example, possible modes of administration and pharmaceutical combination compositions, correspondingly apply to the use of the compound of formula I in combination with conventional cancer therapy.

When using the compound of the formula I, the dose can vary within wide limits and, as is customary, is to be suited to the individual conditions in each individual case. It depends, for example, on the nature and severity of the disease and the general state of the individual to be treated, or on whether an acute or chronic condition is treated or whether prophylaxis is carried out. In the case of oral administration, the daily dose is in general from about 0.01 to about 100 mg/kg, preferably from about 0.1 to about 50 mg/kg, in particular from about 0:1 to about 5 mg/kg, to achieve effective results in an adult weighing about 75 kg (in each case in mg per kg of body weight). Also in the case of intravenous administration the daily dose is in general from about 0.01 to about 100 mg/kg, preferably from about 0.05 to about 10 mg/kg (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

The compound of the formula I can furthermore be employed for diagnostic purposes or as auxiliary in pharmacological or biochemical investigations in which blocking of the vitronectin receptor or influencing of cell-cell or cell-matrix interactions is desired.

EXAMPLES

1) 4-Benzyloxycarbonylcinnamic Acid a) Benzyl 4-formylbenzoate 304 g (2 mol) of 4-formylbenzoic acid were dissolved in 1 l of dimethylformamide (DMF), 304 g (2.2 mol) of potassium carbonate were added and then over a period of 30 min 261 ml (2.2 mol) of benzyl bromide were added at about 40° C. (exothermic reaction). The mixture was stirred for further 4 h at 40° C. to 45° C. Then the reaction mixture was poured into 3 l of ice-water and extracted for times with 1 l each of ethyl acetate. The combined organic layers were dried over sodium sulfate, filtered and the ethyl acetate removed in a rotary evaporator at reduced pressure. 503 g of an oil were obtained. The crude product was used directly in the next reaction step.

b) 4-Benzyloxycarbonylcinnamic Acid 245 g (2.4 mol) of malonic acid were dissolved in 360 ml of pyridine (exothermic, temperature raised to about 50° C.). Then 503 g of the crude benzyl 4-formylbenzoate obtained in step a) and 20 ml of piperidine were added, and the mixture was heated to reflux until the production of carbon dioxide had ceased (about 7 h). The mixture was cooled to room temperature, then 2 l of water were added and the product was precipitated by acidification of the stirred mixture with ca. 600 ml of concentrated hydrochloric acid to pH 1.8 at 10° C. The precipitated product was filtered off, washed with water and dried at 50° C. under reduced pressure. Combined yield of step a) and step b): 529.1 g (97%).

MS (CI): 283.2 (M+H)$^+$.

$^1$H-NMR (DMSO-D$_6$): δ (ppm)=12.58 (s, broad, 1H); 8.02 (d, 2H); 7.85 (d, 2H); 7.65 (d, 1H); 7.55–7.30 (m, 5H); 6.7.0 (d, 1H); 5.38 (s, 2H).

2) Benzyl 4-(2-(pyrimidin-2-ylcarbamoyl)vinyl)benzoate 282.3 g (1 mol) of 4-benzyloxycarbonylcinnamic acid were suspended in 2 l of toluene and 108 ml (1.48 mol) of thionyl chloride were added. The mixture was reacted for about 7 h until the production of sulfur dioxide had ceased and a clear solution of the acid chloride was obtained. The solvent was removed under reduced pressure in a rotary evaporator. The residue was dissolved in 1 l of dichloromethane and added dropwise during 1 h to a solution of 95.2 g (1 mol) of 2-aminopyrimidine and 81 ml (1 mol) of pyridine in 2 l of dichloromethane at 0° C. to 5° C. The reaction mixture was stirred for 1 h at room temperature and then evaporated under reduced pressure in a rotary evaporator. The residue was dissolved in 2.5 l of hot ethanol, then 1.5 l of water were added and the mixture was cooled slowly to 0° C. to 5° C. whereupon the product precipitated. The product was filtered, washed with water and dried at 60° C. under reduced pressure. Yield: 317:1 g (88%).

MS (ES): 360.2 (M+H)$^+$.

$^1$H-NMR (DMSO-D$_6$): δ (ppm)=10.85 (s, broad, H); 8.72 (s, 1H); 8.68 (s, 1H); 8.02 (d, 2H); 7.85 (d, 2H); 7.65 (d, 1H); 7.55–7.18 (m, 7H): 5.38 (s, 2H).

3) 4-(2-(1,4,5,6-Tetrahydropyrimidin-2-ylcarbamoyl)ethyl) benzoic Acid 305 g (0.85 mol) of benzyl 4-(2-(pyrimidin-2-ylcarbamoyl)vinyl)benzoate were hydrogenated in a 20 l B uchi autoclave in 8 l of 20% aqueous acetic acid in the presence of 25 g of 10% palladium/charcoal at, 40° C. under a hydrogen pressure of 2 bar. After 6 h and uptake of 65.76 l of hydrogen the reaction was finished. After standing overnight the mixture was warmed to 70° C. and the catalyst filtered off. The autoclave was washed with 3 l of 20% aqueous acetic acid at 70° C. The catalyst was washed with 1.5 l of 20% aqueous acetic acid at 70° C. The filtrate was evaporated under reduced pressure in a rotary evaporator and the residue was dissolved in 1 l of water with heating. Upon cooling to room temperature the product precipitated. The mixture was cooled to 0° C. to 5° C., the product was filtered off, washed with cold water and dried under reduced pressure at 50° C. Yield: 212 g (90.6%).

MS (ES): 276.1 (M+H)$^+$.

$^1$H-NMR (trifluoroacetic acid): δ (ppm)=11.55 (s); 8.15 (d, 2H); 7.40 (d, 2H); 3.62 (dd, 4H); 3.18 (dd, 2H); 2.95 (dd, 2H); 2.1.5 (m, 2H).

4) 4-(2-(1,4,5,6-tetrahydropyrimidin-2-ylcarbamoyl)ethyl) benzoyl Chloride Hydrochloride 110.2 g (0.4 mol) of 4-(2-(1,4,5,6-tetrahydropyrimidin-2-ylcarbamoyl)ethyl)benzoic acid were suspended in 1.5 l of toluene, then 35 ml of thionyl chloride were added and the mixture was heated to 70° C. for 2 h. Then further 16 ml of thionyl chloride were added and heating was continued until the evolution of sulfur dioxide had ceased. The almost clear solution was evaporated to dryness to give 139.5 g of the crude title compound as a yellow powder. This product was directly used in the subsequent reaction.

MS (FAB): 294.1 ((M+H)$^+$ of the free base).

$^1$H-NMR (CDCl$_3$): δ (ppm)=13.05 (s, broad, 1H); 9.35 (s, broad, 2H); 8.05 (d, 2H); 7.40 (d, 2H); 3.50 (m, 4H); 3.10 (dd, 2H); 2.95 (dd, 2H); 2.05 (m, 2H).

5) (2S)-3-Carbamoyl-2-(naphthalene-1-sulfonylamino) propionic Acid 132.12 g (1 mol) of (S)-asparagine were dissolved in a mixture of 800 ml of water and 500 ml of 2 N sodium hydroxide. Then 500 ml of tetrahydrofuran were added. The mixture was cooled to 0° C., and while keeping the pH at 12.0–12.5 with 2 N sodium hydroxide a solution of 226.7 g (1 mol) of naphthalene-1-sulfonyl chloride in 500 ml of tetrahydrofuran was added within 1 h. The mixture was stirred for 1 h at 0° C. while maintaining the pH at 12.5. Then the mixture was allowed to warm to room temperature, stirred for further 2 h and left at room temperature overnight. The pH was adjusted to about 7 with concentrated hydrochloric acid and the tetrahydrofuran was removed in vakuum in a rotary evaporator. The remaining aqueous solution was cooled to 0° C. and with stirring acidified to pH 0.8 by addition of concentrated hydrochloric acid. After stirring for 30 min at 0° C. the precipitated product was filtered off, washed with water and dried in vacuo at 40° C. Yield: 240 g (75%).

MS (ES): 323.1 (M+H)$^+$.

$^1$H-NMR (DMSO-D$_6$): δ (ppm)=12:50 (s, 1H); 8.65 (d, 1H); 8.35 (d, 1H); 8.20 (d, 1H); 8.17 (d, 1H); 8.09 (d, 1H); 7.80–7.60 (m, 3H); 7.28 (s, 1H); 6.82 (s, 1H); 4.15 (m, 1H); 2.45 (dd, 1H); 2.23 (dd, 1H).

6) (2S-(3-Amino-2-(naphthalene-1-sulfonylamino) propionic Acid

To a stirred solution of 148 g (4.1 mol) of sodium hydroxide in 940 ml of water 26 ml (0.5 mol) of bromine were added over 45 min at 0° C. Then, separately, 129 g (0.4 mol) of (2S)-3-carbamoyl-2-(naphthalene-1-sulfonylamino) succinic acid were dissolved in 400 ml of 2 N sodium hydroxide and further 16 g of sodium hydroxide were added. This solution was cooled to 5° C. and added with vigorous stirring to the previously prepared sodium hypobromite solution while maintaining the temperature of the reaction mixture below 10° C. The mixture was stirred for further 15 min at 10° C. and then warmed within 30 min to 45° C. Then heating was removed and an exothermic reaction proceeded for about 1 h with a peak temperature of about 50° C. When the exothermic reaction had ceased the mixture was heated within 20 min to 70° C. and maintained at this temperature for 10 min. Then the reaction mixture was cooled to 40° C. and at this temperature acidified to pH 6.8 with 330 ml of concentrated hydrochloric acid whereupon the product precipitated. After standing overnight at room temperature, the mixture was cooled to 10° C., the product filtered off, washed with water and dried in vacuuo. Yield: 97.7 g (83%).

MS (FAB): 295.0 (M+H)$^+$.

$^1$H-NMR (DMSO-D$_6$): δ (ppm)=8.58 (d, 1H); 8.25 (d, 2H); 8.09 (d, 1H); 7.90 (s, very broad, 3H); 7.80–7.60 (m, 3H); 3.35 (s, very broad, 2H); 3.18 (m, 1H); 3.05 (dd, 1H); 2.82 (dd, 1H).

7) Ethyl (2S)-3-amino-2-(naphthalene-1-sulfonylamino) propionate Hydrochloride 147.2 g (0.5 mol) of (2S)-3-amino-2-(naphthalene-1-sulfonylamino)propionic acid were suspended in 1 l of ethanol and hydrogen chloride gas was introduced into the mixture for about 2 h whereupon the temperature increased to about 35° C. and a clear solution was obtained. Then the mixture was evaporated in vacuo in a rotary evaporator. The residue was dissolved in hot ethanol and diisopropyl ether was added until precipitation of the product started. The product was allowed to crystallize overnight at room temperature. The title hydrochloride was filtered off, washed with diisopropyl ether and dried in vacuo. Yield: 148 g (83%).

MS (ES): 323.2 ((M+H)$^+$ of the free base).

$^1$H-NMR (DMSO-D$_6$): δ (ppm)=8.95 (s, broad, 1H); 8.63 (d, 1H); 8.40–8.20 (m, 3H); 8.13 (d, 1H); 8.09 (d, 1H); 7.80–7.60 (m, 3H); 4.12 (m, 1H); 3.50–3.36 (m, 2H); 3.08 (dd, 1H); 2.92 (dd, 1H); 0.55 (t, 3H).

8) Ethyl (2S)-2-naphthalene-1-sulfonylamino)-3-(4-(2-(1,4,5,6-tetrahydropyrimidin-2-ylcarbamoyl)ethyl)benzoylamino)propionate Hemifumarate 25.1 g (0.07 mol) of ethyl (2S)-3-amino-2-(naphthalene-1-sulfonylamino)propionate hydrochloride were dissolved in 100 ml of dichloromethane by addition of 17.7 g (0.21 mol) of sodium bicarbonate in 30 ml water. Then under vigourous stirring 23.2 g (0.07 mol) of 4-(2-(1,4,5,6-tetrahydropyrimidin-2-ylcarbamoyl)ethyl)benzoyl chloride hydrochloride were added in portions within 30 min. The reaction mixture was stirred or further 1 h and then the layers were separated. The organic layer was extracted with bicarbonate solution and water and then dried over sodium sulfate. The sodium sulfate was filtered off and washed with dichloromethane. The filtrate was concentrated to about 100 ml and 4.1 g (0.035 mol) of fumaric acid were added to the obtained dichloromethane solution of ethyl (2S)-2-(naphthalene-1-sulfonylamino)-3-(4-(2-(1,4,5,6-tetrahydropyrimidin-2-ylcarbamoyl)ethyl)benzoylamino)propionate. The mixture was heated to reflux until a clear solution was obtained. Upon cooling the title hemifumarate started to precipitate. Precipitation was completed by addition of 300 ml ethyl acetate. The product was collected by filtration, washed with ethyl acetate and dried. Yield: 35.5 g (79.5%). Melting point 201° C.

MS (FAB): 580.3 ((M+H)$^+$ of the free base).

$^1$H-NMR (DMSO-D$_6$): δ (ppm)=9.73 (s, broad, 1H); 8.8 (s, very broad, 1H); 8.63 (d, 1H); 8.33 (t, 1H); 8.16 (d, 1H); 8.09 (d, 1H); 8.01 (d, 1H); 7.72–7.50 (m, 5H); 7.24 (d, 2H); 6.50 (s, 1H); 4.08 (t, 1H); 3.66–3.45 (m, 4H); 3.34 (q, 2H); 3.27 (t, 4H); 2.88 (dd, 2H); 2.59 (dd, 2H); 1.79 (m, 2H); 0.79 (t, 3H).

9) Pharmacological Testing: PTH-Induced Hypercalcemia in the TPTX Rat Model of Bone Resorption In this in vivo model a stimulation of bone resorption is induced in thyroparathyroidectomized (TPTX) rats by the infusion of parathyroid hormone (PTH). The changes in bone resorption are monitored by measuring the serum calcium concentration which is directly related to the extent of bone resorption.

Male Sprague Dawley rats (OFA-IFFA CREDO, France) weighting 150–200 g were thyroparathyroidectomized by the supplier. The rats were allowed free access to a standard commercial pelleted diet containing 7 g Ca/kg (UAR) and Eau de Volvic water. The success of thyroparathyroidectomy was tested by measuring serum calcium concentrations 8 days after operation in overnight fasted animals. Rats were considered as TPTX when the serum calcium level was <80 mg/l.

For treatment with PTH, rat PTH(1–34) (Bachem) was dissolved in 0.15 M sodium chloride solution containing 2% Cys-HCl and delivered via osmotic minipumps (ALZET 2001 D) at 200 pmol/kg/h. The minipumps were inserted into the intraperitoneal cavities under ketamin (75 mg/kg) and acepromazin (2.5 mg/kg) anesthesia in overnight fasted TPTX rats. In the control group TPTX rats received minipumps filled with the vehicle of PTH.

To determine the effect of the compound of formula I, PTH treated TPTX rats were administered twice 10 mg/kg of this compound perorally at time 0 and 3 h after the start of PTH infusion (compound group). In the same manner PTH treated TPTX rats were administered the vehicle (PTH group), and TPTX rats not treated with PTH were administered the vehicle (control group). The experiment was performed for a total of 6 hours. At the end of the treatment protocol, whole blood was collected after decapitation. The blood samples were centrifugated at 3000 rpm for 15 min (CR422 Jouan) to obtain serum.

Serum total calcium concentrations (=calcemia) were measured calorimetrically (Ciba-Corning) using a IEMS Labsystems microplate reader at 540 nm. The differences between the mean values of calcemia in the groups were analysed for variance and by Dunnett's test. The activity of the test compound was calculated as % effect according to the formula:

$$\% \text{ effect} = \frac{\text{Calcemia}_{(compound\ group)} - \text{Calcemia}_{(PTH\ group)}}{\text{Calcemia}_{(PTH\ group)} - \text{Calcemia}_{(control\ group)}} \times 100$$

The % effect observed with the compound of formula I administered perorally twice at 10 mg/kg was −45%. This in vivo result shows that the compound of formula I is a highly efficient inhibitor of bone resorption.

What is claimed is:

1. A process for the preparation of ethyl (2S)-2-(naphthalene-1-sulfonylamino)-3-(4-(2-(1,4,5,6-tetrahydropyrimidin-2-ylcarbamoyl)ethyl)benzoylamino) propionate or a salt thereof, comprising reacting 4-(2-(1,4,5,6-tetrahydropyrimidin-2-ylcarbamoyl)ethyl)benzoic acid or a derivative of the formula

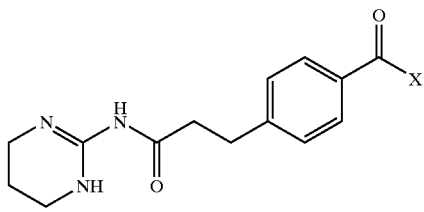

wherein X is hydroxy or a leaving group, with ethyl (2S)-3-amino-2-(naphthalene-1-sulfonylamino)propionate of the formula

III or an acid addition salt or salts of any one or both of the said compounds.

2. The process of claim 1 wherein X is chlorine.

3. The process of claim 1 wherein the reaction product of the compounds of the formalae II and III is reacted with an acid to form the acid addition salt of the compound of the formula

IV

\* \* \* \* \*